United States Patent [19]

Soula et al.

[11] 4,288,386

[45] Sep. 8, 1981

[54] ULLMANN REACTION FOR THE SYNTHESIS OF DIARYL ETHERS

[75] Inventors: Gerard Soula, Meyzieu; Louis Linguenheld, Saint-Genis-Laval, both of France

[73] Assignee: Rhone-Poulenc Industries, Paris, France

[21] Appl. No.: 148,590

[22] Filed: May 12, 1980

[30] Foreign Application Priority Data

May 18, 1979 [FR] France .................................. 79 12688

[51] Int. Cl.³ .................... C07C 41/00; C07C 65/21; C07C 69/94; C07C 121/75
[52] U.S. Cl. ........................ 260/465 F; 260/340.9 R; 260/512 R; 260/512 C; 560/56; 560/64; 560/65; 562/466; 562/473; 562/474; 564/430; 564/504; 564/505; 568/33; 568/52; 568/53; 568/315; 568/433; 568/632; 568/633; 568/634; 568/635; 568/636; 568/637; 568/638; 568/639
[58] Field of Search ............... 260/465 F, 571, 512 R, 260/340.9 R; 568/635, 636, 637, 638, 639, 33, 52, 315, 433, 632–634; 560/64; 562/473; 564/430

[56] References Cited

U.S. PATENT DOCUMENTS 3,083,234 3/1963 Sax ..................................... 568/636

FOREIGN PATENT DOCUMENTS 1302365 7/1962 France .
1052390 12/1966 United Kingdom .

*Primary Examiner*—Dolph H. Torrence
*Attorney, Agent, or Firm*—Burns, Doane, Swecker & Mathis

[57] ABSTRACT

The Ullman reaction for the preparation of diaryl ethers by coupling aryl halides with metal phenolates is conducted in the presence of at least one tertiary amine sequestering agent having the formula:

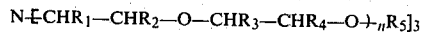

$$N\text{-}[CHR_1\text{---}CHR_2\text{---}O\text{---}CHR_3\text{---}CHR_4\text{---}O)_n R_5]_3$$

26 Claims, No Drawings

ULLMANN REACTION FOR THE SYNTHESIS OF DIARYL ETHERS

BACKGROUND OF THE INVENTION

1. Field of the Invention

The present invention relates to an improved process for the preparation of diaryl ethers and, more especially, to a process for the preparation of diaryl ethers by reacting an unactivated halobenzene with a phenolate or a naphtholate [hereinafter collectively designated simply as "phenolate"] in the presence of a copper catalyst.

Description of the Prior Art

The aforenoted basic reaction is very well known to the prior art; it is the Ullmann synthesis of ethers, comprising reacting an unactivated halobenzene (i.e., a halobenzene which does not contain, in the position ortho- or para- to the halo group, a group which selectively activates said ortho- and para-positions) with a phenolate, in the presence of a copper compound as a catalyst.

More particularly, British Patent Specification No. 1,052,390 describes the reaction of potassium m-cresolate with bromobenzene, in the presence of activated copper bronze, to obtain 3-phenoxytoluene. Such reaction takes place in bromobenzene at 220° C.–240° C. The main disadvantage of this type of process is that it requires a large amount of the brominated derivative, the latter being used both as a reactant and as the solvent. It too is well known to the art, though, that said brominated derivative is quite expensive. And the high temperature at which the reaction takes place constitutes a further major disadvantage.

Nonetheless, processes do exist which make it possible to utilize the chlorinated derivative. In particular, compare published Japanese Patent Application No. 72/104,672; this publication describes a process for the preparation of meta-phenoxy-toluene, in accordance with which process an alkali metal salt of meta-cresol is reacted with chlorobenzene, in the presence of organic bases, with copper powder or copper compounds being used as a catalyst. The reaction takes place in quinoline at temperatures on the order of 200° C. The great disadvantage of this process, as regards its application on an industrial scale, is no doubt the fact that a solvent such as quinoline involves numerous drawbacks which result from the difficulties encountered in its use and from its high price.

Another published Japanese Patent Application, namely, Application No. 77/035,128, features a process which makes it possible to react chlorobenzene with m-cresolate, in the presence of copper or copper compounds, but in the absence of a solvent.

Utilization of this particular process on an industrial scale, however, presents many serious problems because it must be carried out under pressure and at high temperatures (200°–250° C.).

It will thus be seen that, as regards the preparation of diaryl ethers by reacting an unactivated halobenzene with a phenolate, in the presence of a copper compound, the prior art has yet to provide for a facile and conventional application of the Ullmann reaction on an industrial scale. The requirements which to date have not been met by the prior art can be analyzed in terms of three different points, taken either alone or in any combination. The first concerns the solvent: it would be desirable to be able to use, industrially, solvents which have a low toxicity, as well as good thermal and chemical stability, without at the same time detracting from the economics of the process; in particular, it would be advantageous, in numerous cases, to be able to use one of the reactants as the solvent. The second point concerns the reaction temperature: it is clear that lowering the reaction temperature would constitute a very appreciable advantage both from a technical point of view and also from an economic point of view. In particular, the need to carry out the reaction at the lowest possible temperatures, in the case where the reactants or the products obtained are thermally sensitive to thermal effects, must be emphasized. The third point concerns the halobenzene: as is apparent from the foregoing text, it would be desirable to be able to replace the brominated derivatives by the corresponding chlorinated derivatives under similar reaction conditions.

SUMMARY OF THE INVENTION

Accordingly, a major object of the present invention is the provision of an improved Ullmann reaction which meets all of the aforesaid desiderata.

Briefly, the present invention features a process for the preparation of a diaryl ether by reacting an unactivated halobenzene with an alkali metal phenolate, in the presence of a copper catalyst, the improvement comprising conducting the reaction in the presence of at least one sequestering agent having the structural formula:

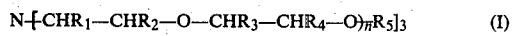

$$N-[CHR_1-CHR_2-O-CHR_3-CHR_4-O)_nR_5]_3 \quad (I)$$

in which n is an integer which is greater than or equal to 0 and less than or equal to about 10 ($0 \leq n \leq 10$), $R_1$, $R_2$, $R_3$ and $R_4$, which are identical or different, each represent a hydrogen atom or an alkyl radical having from 1 to 4 carbon atoms and $R_5$ represents an alkyl or cycloalkyl radical having from 1 to 12 carbon atoms, a phenyl radical or a radical $-C_mH_{2m}-\phi$ or $C_mH_{2m+1}-\phi-$, in which m is between 1 and 12 ($1 \leq m \leq 12$).

The reaction, moreover, can take place either in the absence or in the presence of a solvent.

DETAILED DESCRIPTION OF THE INVENTION

More particularly according to this invention, it has now been determined that the sequestering agent of the formula (I) forms, on the one hand with the copper compound, and on the other hand with the alkali metal phenolate, complexes which are soluble in the reaction medium, whereas the copper compound and the phenolate, in uncomplexed form, are either insoluble or very sparingly soluble in said medium. Such complexation exhibits a dual effect; first, it permits the solubilization of the catalyst and the phenolate and thus enables the reaction to in fact take place; secondly, although not yet completely understood in detail, it would appear that the complexation activates the reaction system in such a way that the reaction takes place under much milder conditions than those of the prior art. Thus, the reaction is carried out at relatively low temperatures and under atmospheric pressure, even when utilizing the chlorinated derivative. Of course, the invention is equally applicable to the other halobenzenes, such as, for example, the bromobenzenes, although the industrial value under these circumstances is less pronounced in the majority of cases.

If the reaction is carried out without a solvent, the copper compound complexed by the sequestering agent and the alkali metal phenolate complexed by the same sequestering agent are soluble in the halobenzene, the sequestering agent itself being soluble in the halobenzene.

If the reaction is carried out in the presence of a solvent, the copper compound complexed by the sequestering agent, the phenolate complexed by the sequestering agent and the halobenzene are soluble in the solvent in question, the sequestering agent itself being soluble in said solvent.

A preferred embodiment of the invention features use of sequestering agent of the formula (I) in which $R_1$, $R_2$, $R_3$ and $R_4$ represent a hydrogen atom or a methyl radical, $R_5$ and n being as above defined.

Among such sequestering agents, the use of those in which n is greater than or equal to 0 and less than or equal to 6, and in which $R_5$ represents an alkyl radical having from 1 to 4 carbon atoms, is even more preferred.

The following sequestering agents are noted as illustrative:

[1] tris-(3oxabutyl)-amine of the formula:

$$N-(CH_2-CH_2-O-CH_3)_3$$

[2] tris-(3,6-dioxaheptyl)-amine of the formula:

$$N-(CH_2-CH_2-O-CH_2-CH_2-O-CH_3)_3$$

[3] tris-(3,6,9-trioxadecyl)-amine of the formula:

$$N-(CH_2-CH_2-O-CH_2-CH_2-O-CH_2-CH_2-O-CH_3)_3$$

[4] tris-(3,6-dioxaoctyl)-amine of the formula:

$$N-(CH_2-CH_2-O-CH_2-CH_2-O-C_2H_5)_3$$

[5] tris-(3,6,9-trioxaundecyl)-amine of the formula:

$$N-(CH_2-CH_2O-CH_2-CH_2-O-CH_2-CH_2-O-C_2H_5)_3$$

[6] tris-(3,6-dioxanonyl)-amine of the formula:

$$N-(CH_2-CH_2-O-CH_2-CH_2-O-C_3H_7)_3$$

[7] tris-(3,6,9-trioxadodecyl)-amine of the formula:

$$N-(CH_2-CH_2-O-CH_2-CH_2-O-CH_2-CH_2O-C_3H_7)_3$$

[8] tris-(3,6-dioxadecyl)-amine of the formula:

$$N-(CH_2-CH_2-O-CH_2-CH_2-O-C_4H_9)_3$$

[9] tris-(3,6,9-trioxatridecyl)-amine of the formula:

$$N-(CH_2-CH_2-O-CH_2-CH_2-O-CH_2-CH_2-O-C_4H_9)_3$$

[10] tris-(3,6,9,12-tetraoxatridecyl)-amine of the formula:

$$N-[CH_2-CH_2-O-(CH_2-CH_2-O)_3-CH_3]_3$$

[11] and tris-(3,6,9,12,15,18-hexaoxanonadecyl)-amine of the formula:

$$N-[CH_2-CH_2-O-(CH_2-CH_2-O)_5-CH_3]_3$$

The following sequestering agents are also representative:

[12] tris-(3,6-dioxa-4-methylheptyl)-amine of the formula:

$$N-(CH_2-CH_2-O-\underset{\underset{CH_3}{|}}{CH}-CH_2-O-CH_3)_3$$

and [13] tris-(3,6-dioxa-2,4-dimethylheptyl)-amine of the formula:

$$N-(CH_2-\underset{\underset{CH_3}{|}}{CH}-O-\underset{\underset{CH_3}{|}}{CH}-CH_2-O-CH_3)_3$$

The amine sequestering agents utilized in the process according to the invention are per se known to the prior art. Thus, French Patent No. 1,302,365 describes the preparation of the tertiary amines $N-(CH_2-CH_2-O-CH_3)_3$ and $N-(CH_2-CH_2-O-CH_2-CH_2-O-CH_3)_3$ as by-products from the synthesis of the corresponding primary and secondary amines, such primary and secondary amines being valuable as intermediates in the synthesis of various pharmaceuticals, as corrosion inhibitors, as intermediates in the synthesis of agricultural chemicals, and as emulsifiers. It will also be appreciated, though, that the prior art, including the aforenoted French Pat. No. 1,302,365, is conspicuously devoid of any suggestion that the topic amines could be utilized in an Ullmann reaction consistent with this invention.

The process according to the invention is applicable to the reaction of a halobenzene having the structural formula:

in which n is greater than or equal to 1 and less than or equal to 6 ($1 \leq n \leq 6$), the radical or radicals X, which are identical or different, are selected from the group comprising Cl, Br and I, and the radical or radicals $R_6$, which are identical or different, are selected from the group comprising hydrogen, alkyl and cycloalkyl radicals having from 1 to 12 carbon atoms, alkenyl radicals having from 3 to 12 carbon atoms, such as, for example, propenyl, nonyl and dodecyl radicals, the radicals of the formulae $C_mH_{2m+1}-\phi-$, $C_mH_{2m}-1-\phi-$ and $\phi-C_mH_{2m}-$, in which m is an integer between 1 and 12 ($1 \leq m \leq 12$) and in which the phenyl moiety $\phi$ can either be substituted or unsubstituted, alkoxy radicals having from 1 to 12 carbon atoms and phenoxy radicals, the radicals $-C_mH_{2m}-OH$ and $-C_mH_{2m}OR$, in which m is an integer between 1 and 12 ($1 \leq m \leq 12$) and in which R is an alkyl radical having from 1 to 12 carbon atoms or a phenyl radical, alkylthio radicals having from 1 to 12 carbon atoms and phenylthio radicals, the radicals $C_pH_{2p+1-q}F_q$, p being between 1 and 4

($1 \leq p \leq 4$) and q being between 3 and 9 ($3 \leq q \leq 9$), such as, for example, —$CF_3$ and —$CH_2$—$CF_3$, the radicals

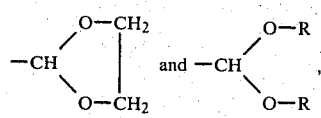

in which R is an alkyl radical having from 1 to 12 carbon atoms or a phenyl radical, and the radicals —$NO_2$, —$SO_3M$, —CN, —$CO_2M$, —$CO_2R$, —COR and —COH, in which M represents an alkali metal and in which R represents an alkyl radical having from 1 to 12 carbon atoms or a phenyl radical.

If $R_6$ is in the ortho- or para-position relative to a substituent X, same cannot represent one of the radicals —$NO_2$, —$SO_3M$, —CN, —$CO_2M$, —$CO_2R$, —COR and —$SO_2R$ defined above, these radicals in fact selectively activating such ortho- and para-positions.

The phenolates which can be utilized in the process of the invention have the structural formula:

$$Ar(O^{-M+})_r \qquad (III)$$

in which Ar represents an optionally substituted phenyl or naphthyl radical, $M^+$ represents a cation selected from the group comprising cations derived from alkali metals and r is an integer between 1 and 3 ($1 \leq r \leq 3$).

More particularly, the invention relates to the reaction of compounds having the structural formulae:

in which r is equal to 1 or 2, the cation or cations $M^+$, which are identical or different, are selected from the group comprising $Li^+$, $Na^+$ and $K^+$, and the radical or radicals $R_7$, which are identical or different, are selected from the group comprising hydrogen, alkyl and cycloalkyl radicals having from 1 to 12 carbon atoms, alkenyl radicals having from 3 to 12 carbon atoms, such as, for example, propenyl, nonyl and dodecyl radicals, the radicals of the formulae $C_mH_{2m+1}\phi$—, $C_mH_{2m-1}\phi$— and $\phi$—$C_mH_{2m}$—, in which m is an integer between 1 and 12 ($1 \leq m \leq 12$) and in which the phenyl moiety $\phi$ can either be substituted or unsubstituted, alkoxy radicals having from 1 to 12 carbon atoms and phenoxy radicals, the radicals —$C_mH_{2m}$—OH and —$C_mH_{2m}OR$, in which m is an integer between 0 and 12 ($0 \leq m \leq 12$) and in which R is an alkyl radical having from 1 to 12 carbon atoms or a phenyl radical, alkylthio radicals having from 1 to 12 carbon atoms and phenylthio radicals, the radicals $C_pH_{2p+1-q}F_q$, p being between 1 and 4 ($1 \leq p \leq 4$) and q being between 3 and 9 ($3 \leq q \leq 9$), such as, for example, —$CF_3$ and —$CH_2$—$CF_3$, the radicals

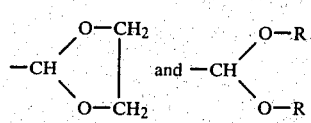

in which R is an alkyl radical having from 1 to 12 carbon atoms or a phenyl radical, the radicals Cl and F and the radicals —$NO_2$, —$NH_2$, —NHR, —NRR, —$SO_3M$, —CN, —$CO_2M$, —$CO_2R$, —COR, —COH and —$SO_2R$, in which M represents an alkali metal and in which R represents an alkyl radical having from 1 to 12 carbon atoms or a phenyl radical.

The invention relates more particularly, but not exclusively, to the reaction of a compound of the formula II which only contains one substituent X with a compound of the formula III which only contains one substituent $O^{-M+}$, and also to the reaction of a compound of the formula II which contains one substituent X with a compound of the formula III which contains a plurality of substituents $O^{-M+}$, and vice versa, namely, the reaction of a compound of the formula II which contains a plurality of substituents X which a compound of the formula III which contains one substituent $O^{-M+}$.

The following compounds are set forth as exemplary of the halobenzenes of the formula II:

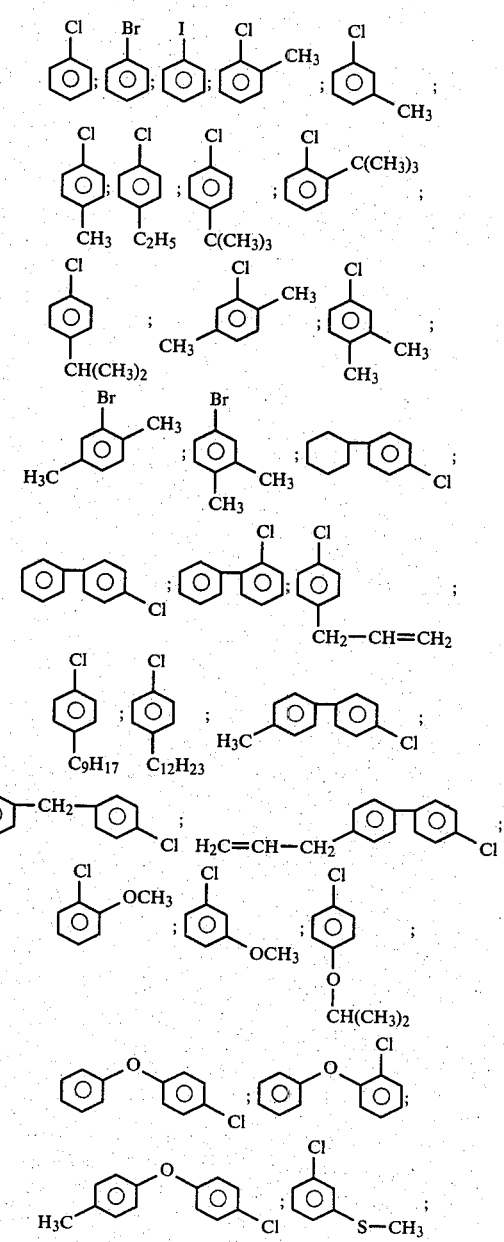

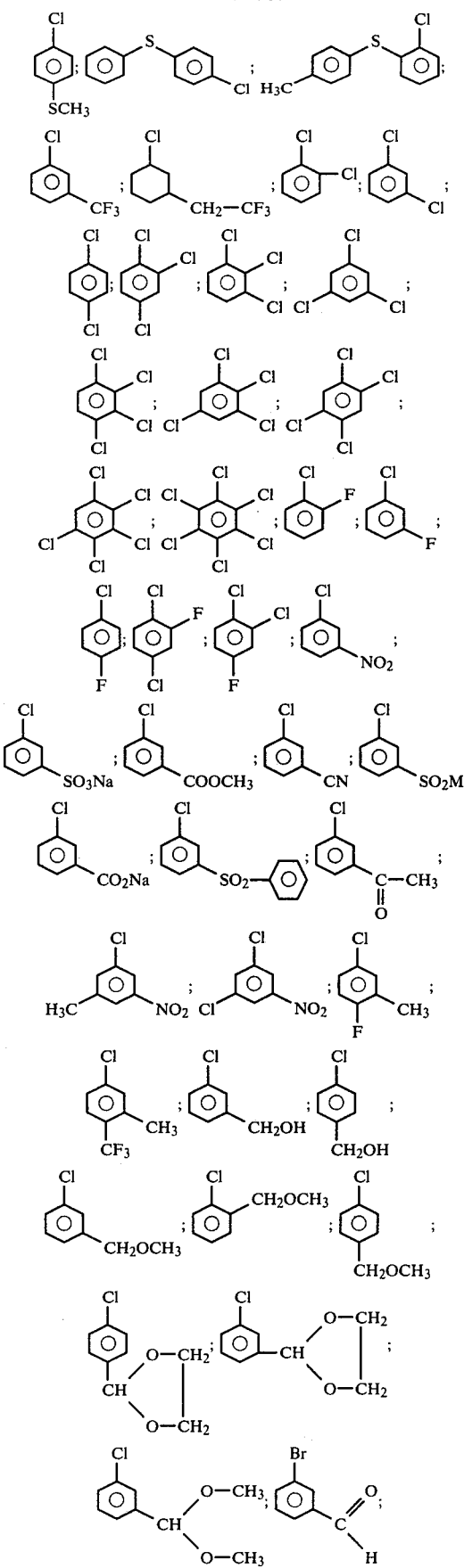
-continued
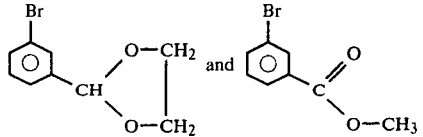
The following phenols and naphthols are exemplary of the phenolates of the structural formulae IIIa and IIIb:
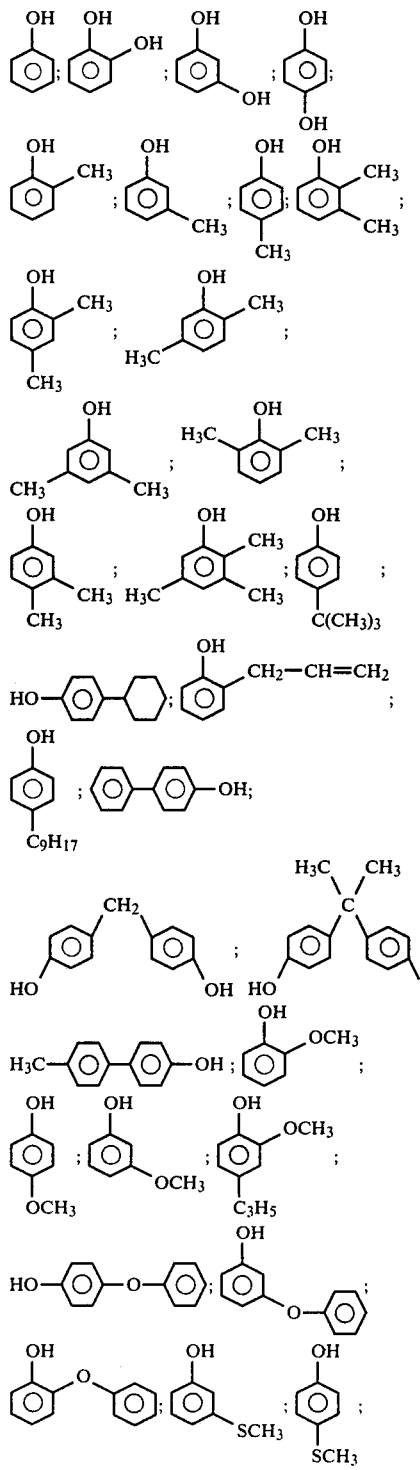

-continued

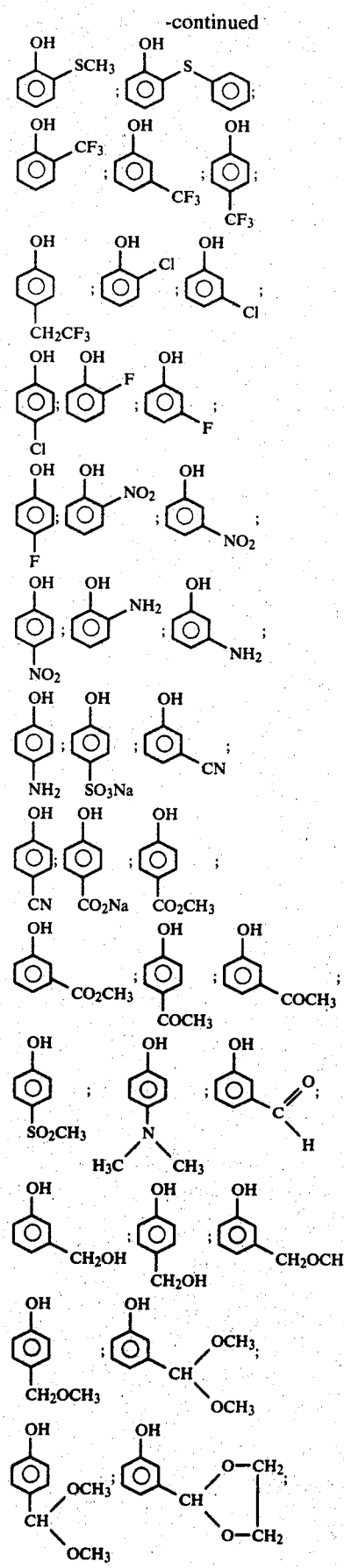

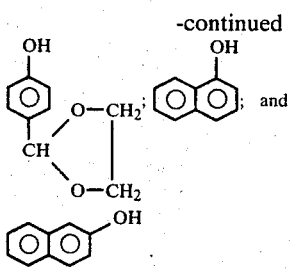

The selection of the most suitable sequestering agent for carrying out the process according to the invention is advantageously made with regard to the size of the cation $M^+$. The greater the size of the cation, the greater should be the number of oxygen atoms present in the molecule of the sequestering agent. Thus, if a potassium phenolate is used, tris-(3,6,9-trioxadecyl)-amine is preferred, whereas tris-(3,6-dioxaheptyl)-amine is preferred in the case of the corresponding sodium salt.

If a solvent is used, it must satisfy a certain number of conditions; firstly, it must solubilize the sequestering agent (the latter being soluble in the majority of the typical solvents); it must also be chemically inert visavis the salts to be dissolved. It must also be noted that, in order to obtain the best results according to the invention, the more pronounced the apolar character of the selected solvent, the more pronounced must be the lipophilic character of the sequestering agent (namely, the greater must be the number of carbon atoms present in the sequestering agent).

Examples of solvents which can be utilized are diphenyl ether, anisole, toluene, glycol polyethers, benzene and the xylenes.

The copper compounds which can be used as catalysts are also per se known to the prior art. The following compounds are exemplary: $CuCl$, $CuBr$, $CuI$, $CuOCOCH_3$ and $Cu_2O$. In a preferred embodiment, $CuCl$ or $CuBr$ is utilized.

The process according to the invention is characteristically carried out at a temperature between about 50° C. and 200° C. It is preferably carried out at a temperature between about 100° and about 180° C.

As noted hereinabove, the process is typically carried out at atmospheric pressure. Of course, pressures below or above atmospheric pressure are not excluded by the present invention.

The amount of sequestering agent employed is such that the molar ratio of the copper compound to the sequestering agent of the formula I is preferably between about 0.05 and 10. This ratio is more preferably between about 0.1 and 5.

The molar ratio of the copper compound to the phenolate is preferably between about 0.005 and about 0.15. It is more preferably between about 0.01 and 0.1.

The molar ratio of the halobenzene to the phenolate is preferably between about 0.8 and about 50. More preferably, this ratio is between about 0.9 and about 30. The high values of this ratio correspond to the case where the halobenzene is also used as the solvent.

The diaryl ethers prepared consistent with the present invention have the following structural formulae IV:

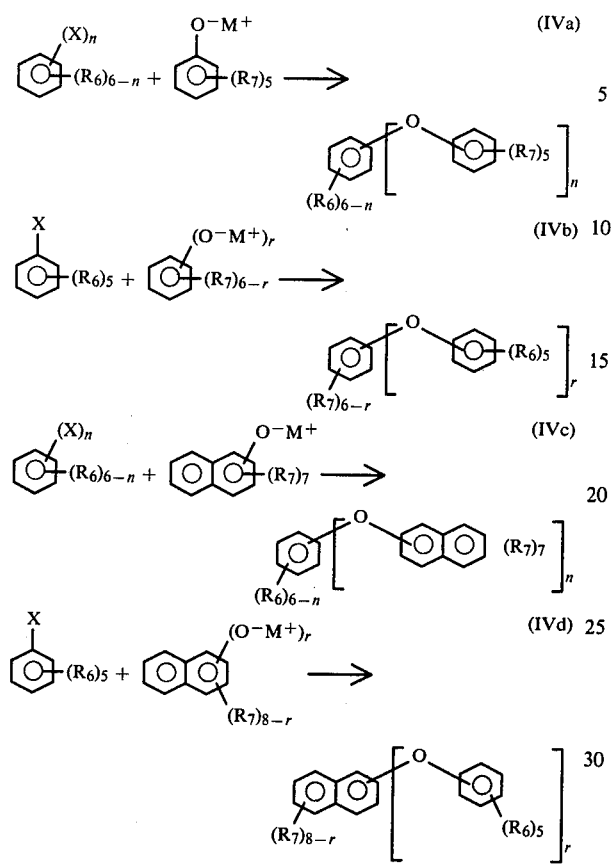

The following diaryl ethers are exemplary of compounds of the formula IV:

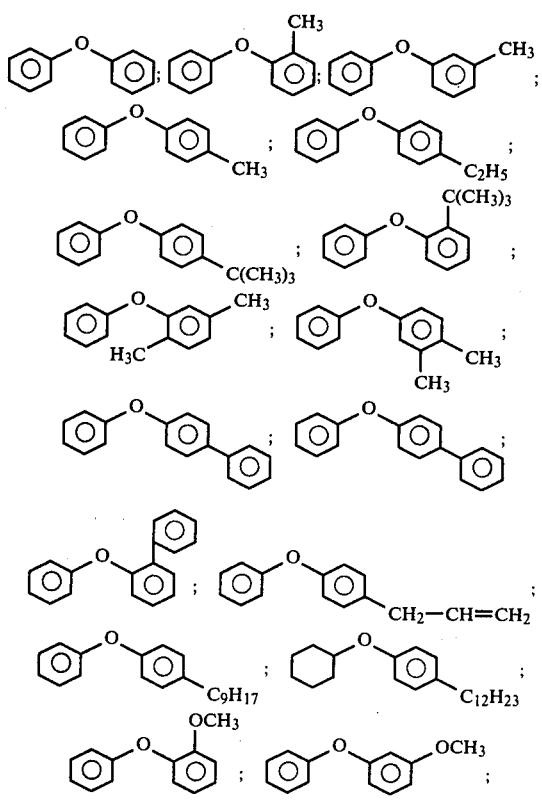

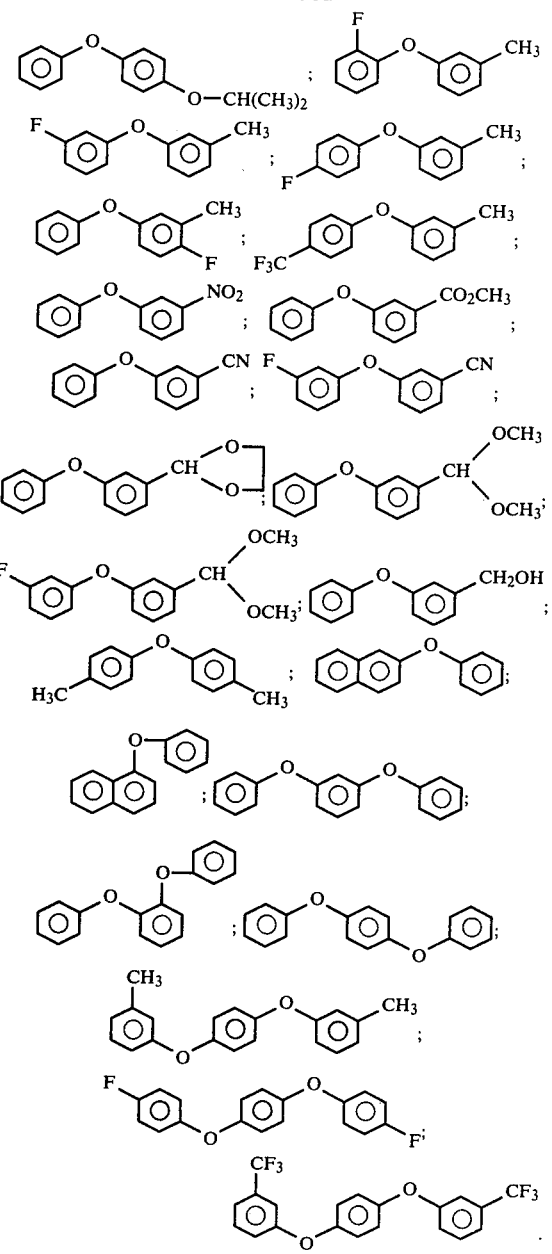

The subject diaryl ethers are notable intermediates for the synthesis of compounds useful in plant husbandry, and also for the preparation of a wide variety of pharmaceuticals.

The sequestering agents of the formula I employed in the process according to the invention can be prepared by condensing a salt having the structural formula:

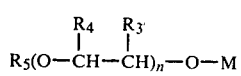

in which $R_3$, $R_4$, $R_5$ and n are as above defined and in which M represents an alkali metal atom selected from among the group comprising sodium, potassium and lithium, either with an amine having the structural formula:

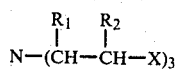

in which $R_1$ and $R_2$ are as above defined and X represents chlorine or bromine, or with the corresponding hydrochloride or hydrobromide thereof.

The molar ratio alkali metal salt/amine desirably is between about 3 and about 5.

The condensation is carried out at a temperature between 100° and 150° C. for 1 to 15 hours, in the presence of a solvent which can be, for example, chlorobenzene or, preferably, the ethylene glycol monoalkyl ether having the formula $R_5—(O—CHR_4—CHR_3)_n—OH$.

The process is preferably carried out in such manner that the solution contains from 2 to 5 mols of alkali metal salt per liter of solvent.

Upon completion of the reaction, the mixture essentially consists of the tertiary amine of the formula:

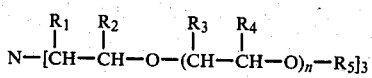

but also contains a small proportion of the corresponding secondary amine:

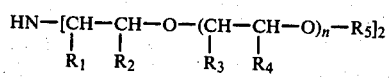

and traces of the primary amine:

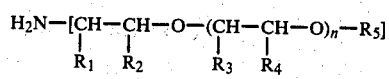

The tertiary, secondary and primary amines are typically present in the admixture of reaction in the ratio 90:8:2, respectively, after distillation.

In the process according to the invention, the aforenoted reaction mixture obtained after a first distillation, i.e., the mixture containing the three different types of amine, can be directly utilized.

To obtain better results consistent with the invention, it is preferred to carry out a more thorough distillation of the above mixture in order to obtain essentially pure tertiary amine.

In order to further illustrate the present invention and the advantages thereof, the following specific examples are given, it being understood that same are intended only as illustrative and in no wise limitative.

EXAMPLE 1

Preparation of meta-phenoxytoluene,

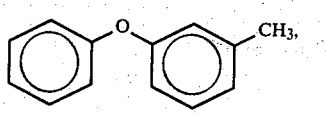

from sodium meta-cresolate,

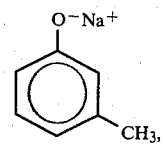

and chlorobenzene,

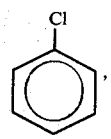

in the presence of cuprous chloride, CuCl, and either:

(a) In the presence of tris-(3,6-dioxaoctyl)amine having the formula $N–(CH_2—CH_2—O—CH_2—O—C_2H_5)_3$:

216 g (2 mols) of meta-cresol, 80 g (2 mols) of sodium hydroxide, 60 g of water and 1,250 g (11 mols) of chlorobenzene were introduced into a two liter three-necked round-bottomed flash equipped with a stirrer, a thermometer, a dropping funnel and a fraction separator. The mixture was then heated to 133° C. and the water was distilled as an azeotrope. The sodium cresolate slurry was fluid at 135° C. At this point, a stream of inert gas (nitrogen) was blanketed therein and 18 g (0.18 mol) of cuprous chloride and 38 g (0.104 mol) of tris-(3,6-dioxaoctyl)-amine were added thereto. Reflux was maintained for 6 hours and the progress of the reaction was chromatographically monitored by testing for the disappearance of the chlorobenzene and the appearance of the phenoxy-toluene. After 6 hours at 135° C., the degree of conversion was 89% and the yield was 97%.

After cooling, the sodium chloride was extracted with acid water and then with alkaline water and the organic mixture was distilled to give 302 g of meta-phenoxytoluene; boiling point 5:120° C., $d_4^{20}$:1.045.

(b) In the presence of tris-(3,6-dioxaheptyl)amine having the formula $N–(CH_2—CH_2—O—CH_2—CH_2—O—CH_3)_3$:

216 g (2 mols) of meta-cresol, 60 g (1.5 mols) of sodium hydroxide, 28 g (0.5 mol) of potassium hydroxide, 60 g of water and 1,250 g (11 mols) of chlorobenzene were introduced into the same equipment as above. Salt formation was carried out as in Example 1(a), and then, after having placed the mixture under a blanket of hydrogen, 17 g (0.17 mol) of cuprous chloride and 30 g (0.093 mol) of tris-(3,6-dioxaheptyl)-amine were added thereto. Reflux was maintained for 6 hours and the progress of the reaction was monitored. After this period had elapsed, the degree of conversion of the cresol had reached 90% and the yield had reached 97%.

COMPARATIVE EXAMPLE:

The above procedure was repeated except that no sequestering agent according to the invention was added. After 6 hours, the degree of completion of the reaction was only 5% and it was necessary to reflux for 106 hours in order to obtain a degree of conversion of 50%.

EXAMPLE 2

Preparation of meta-phenoxytoluene,

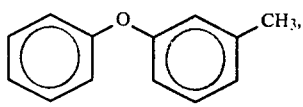

from sodium phenolate,

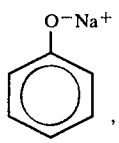

and 3-chlorotoluene,

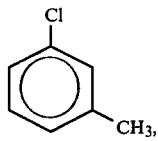

in the presence of cuprous chloride, CuCl, and tris-(3,6-dioxaoctyl)-amine, N—(CH$_2$—CH$_2$—O—CH$_2$—CH$_2$—O—C$_2$H$_5$)$_3$.

1.16 g (0.01 mol) of sodium phenate, 20 g (0.158 mol) of 3-chlorotoluene, 0.099 g (0.001 mol) of cuprous chloride and 0.36 g (0.001 mol) of tris-(3,6-dioxaoctyl)amine were introduced into a 100 cm$^3$ Erlenmeyer flask which was equipped with a magnetic stirring bar and was maintained under a blanket of nitrogen. After refluxing for 4 hours, the degree of conversion had reached 91%.

COMPARATIVE EXAMPLE:

The above procedure was repeated, except that no tris-(3,6-dioxaoctyl)-amine was added. After refluxing for 4 hours, the degree of conversion had reached 0.6%.

EXAMPLE 3

Preparation of ortho-phenoxytoluene,

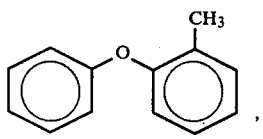

from sodium ortho-cresolate,

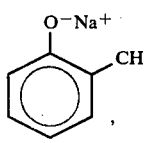

and chlorobenzene,

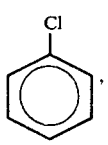

in the presence of cuprous chloride, CuCl, and tris-(3,6-dioxaoctyl)-amine, N—(CH$_2$—CH$_2$—O—CH$_2$—CH$_2$—O—C$_2$H$_5$)$_3$.

1.30 g (0.01 mol) of sodium ortho-cresolate, 20 g (0.18 mol) of chlorobenzene, 0.099 g (0.001 mol) of cuprous chloride and 0.36 g (0.001 mol) of tris-(3,6-dioxaoctyl)amine were introduced into a 100 cm$^3$ Erlenmeyer flask equipped with a magnetic stirring bar. After refluxing for 6 hours, the degree of conversion had reached 92%.

COMPARATIVE EXAMPLE:

The above procedure was repeated, except that no tris-(3,6-dioxaoctyl)-amine was added. After refluxing for 6 hours, the degree of conversion was only 1.2%.

EXAMPLE 4

Preparation of 1,2-diphenoxybenzene,

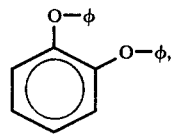

from sodium phenolate, $\phi$—O$^-$Na$^+$, and ortho-dichlorobenzene,

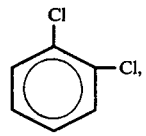

in the presence of cuprous chloride and tris-(3,6-dioxaoctyl)-amine.

2.32 g (0.002 mol) of sodium phenate, 1.47 g (0.01 mol) of o-dichlorobenzene, 0.2 g (0.002 mol) of cuprous chloride and 0.72 g (0.002 mol) of tris-(3,6-dioxaoctyl)amine in 20 g of anisole were introduced into a 100 ml Erlenmeyer flask equipped with a magnetic stirring bar. After refluxing for 20 hours, the degree of conversion was 60% with respect to 1,2-diphenoxybenzene and 5% with respect to 1-chloro-2-phenoxybenzene.

COMPARATIVE EXAMPLE:

The above procedure was repeated except that no tris-(3,6-dioxaoctyl)-amine was added; the degree of conversion was zero after 20 hours at the reflux temperature of the anisole.

EXAMPLE 5

Preparation of 2-(3'-methylphenoxy)-fluorobenzene,

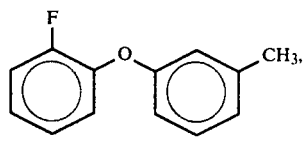

from 1-chloro-2-fluorobenzene,

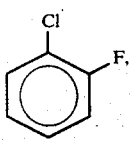

and sodium meta-cresolate,

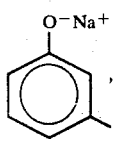

in the presence of cuprous chloride, CuCl, and tris-(3,6-dioxaoctyl)-amine.

20 g (0.15 mol) of 1-chloro-2-fluorobenzene, 1.37 g (0.01 mol) of sodium m-cresolate, 0.099 g (0.001 mol) of copper chloride and 0.36 g (0.001 mol) of tris-(3,6-dioxaoctyl)-amine were introduced into a 100 ml Erlenmeyer flask which was equipped with a magnetic stirring bar and was maintained under a stream of hydrogen. The mixture was heated under reflux for 24 hours. The degree of conversion with respect to 1-fluoro-2-(3'-methylphenoxy)-benzene had reached 75%.

COMPARATIVE EXAMPLE

The above procedure was repeated, except that no tris-(3,6-dioxaoctyl)-amine was added. The degree of conversion was 11% after refluxing for 24 hours.

EXAMPLE 6

Preparation of 3-(3'-fluorophenoxy)-toluene,

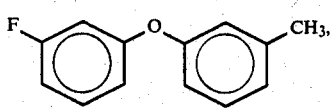

from 3-chlorotoluene,

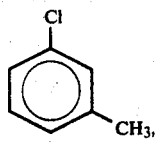

and sodium meta-fluorophenolate,

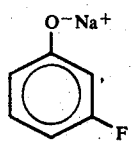

in the presence of cuprous chloride, CuCl, and tris-(3,6-dioxaoctyl)-amine.

110 g (0.87 mol) of 3-chlorotoluene, 8 g (0.06 mol) of sodium meta-fluorophenate, 0.6 g (0.006 mol) of cuprous chloride and 2.2 g (0.006 mol) of tris-(3,6-dioxaoctyl)-amine were introduced into a 500 ml round-bottomed flask which was equipped with a stirrer and heated by an oil bath. The mixture was heated for 8 hours, 30 minutes, under reflux (180° C.). The degree of conversion with respect to m-(3'-fluorophenoxy)-toluene had then reached 65.9%.

COMPARATIVE EXAMPLE

The above procedure was repeated, except that no sequestering agent was added; the degree of conversion was 5%.

EXAMPLE 7

Preparation of meta-phenoxybenzonitrile,

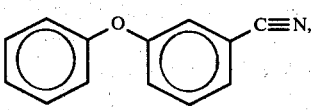

from 3-chlorobenzonitrile,

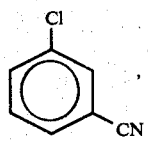

and sodium phenolate,

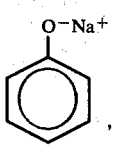

in the presence of cuprous chloride, CuCl, and tris-(3,6-dioxaoctyl)-amine and (a) In the presence of anisole:

100 g (0.73 mol) of 3-chlorobenzonitrile, 98 g (0.84 mol) of sodium phenate, 7.2 g (0.072 mol) of cuprous chloride, 10.3 g (0.028 mol) of tris-(3,6-dioxaoctyl)-amine and 570 g of anisole were introduced into a 1 liter round-bottomed flask equipped as in Example 1. The mixture was then heated under reflux (155° C.) for 6 hours, under a nitrogen atmosphere. The degree of conversion was 85% and the yield with respect to distilled m-phenoxybenzonitrile was 70%.

(b) In the presence of diphenyl ether:

The procedure set forth under (a) was repeated, except that the anisole was replaced by phenyl ether, and this enabled heating the mixture at 180° C. for 6 hours. The degree of conversion was then 95% and the yield with respect to distilled m-phenoxybenzonitrile was 70%.

COMPARATIVE EXAMPLE

The procedure set forth under (b) was repeated except that no tris-(3,6-dioxaoctyl)-amine was added. The degree of conversion after 6 hours was 15%.

EXAMPLE 8

Preparation of meta-phenoxybenzonitrile,

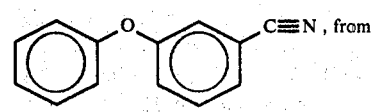

-continued

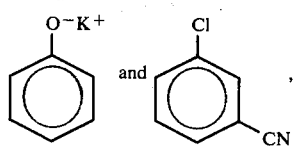

in the presence of cuprous chloride, CuCl, and tris-(3,6,9-trioxadecyl)-amine.

192 g (3.43 mols) of potassium hydroxide, 252 g of water, 320 g (3.8 mols) of phenol and 675 g of anisole were introduced into a 3 liter round-bottomed flask equipped as in Example 1. Salt formation was carried out by heating the mixture under reflux in order to remove the water as an azeotrope. The equipment was then placed under a nitrogen blanket and 460 g (3.34 mols) of chlorbenzonitrile dissolved in 500 g of anisole, 36 g (0.36 mol) of cuprous chloride and 26 g (0.057 mol) of tris-(3,6,9-trioxadecyl)-amine were introduced. Reflux (140° C.) was maintained for 6 hours; the degree of conversion had reached 80%.

After cooling the mixture, the chlorides were extracted with acidified water and, after separating off the aqueous layer by decantation, the anisole, the unreacted phenol and the m-phenoxybenzonitrile (boiling point $_{0.5}$:127° C., yield: 73%) were recovered by distillation.

EXAMPLE 9

Preparation of meta-phenoxynitrobenzene,

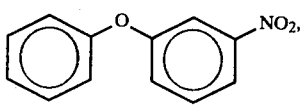

from meta-chloronitrobenzene,

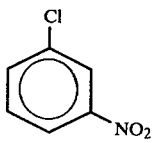

and sodium phenolate,

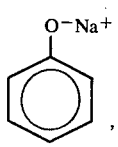

in the presence of cuprous chloride, CuCl, and tris-(3,6-dioxaoctyl)-amine.

7.9 g (0.05 mol) of m-chloronitrobenzene, 5.8 g (0.05 mol) of sodium phenate, 0.5 g (0.005 mol) of cuprous chloride and 1.85 g (0.005 mol) of tris-(3,6-dioxaoctyl)-amine in 50 cm³ of anisole were introduced into a 100 cm³ Erlenmeyer flask which was equipped with a magnetic stirring bar and was under a nitrogen atmosphere. The mixture was heated under reflux for 6 hours. The degree of conversion had then reached 72%.

COMPARATIVE EXAMPLE

The degree of conversion was only 12% when the above process was carried out without adding the tris-(3,6-dioxaoctyl)-amine.

EXAMPLE 10

Preparation of methyl meta-phenoxybenzoate,

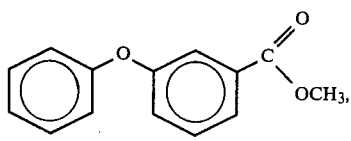

from sodium phenolate,

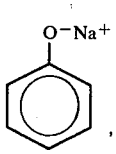

and methyl meta-chlorobenzoate,

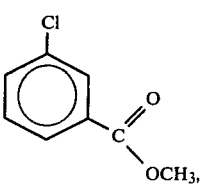

in the presence of cuprous chloride, CuCl, and tris-(3,6-dioxaoctyl)-amine.

17.1 g (0.098 mol) of methyl meta-chlorobenzoate, 11.6 g (0.1 mol) of sodium phenate, 1 g (0.001 mol) of cuprous chloride and 3.7 g (0.001 mol) of tris-(3,6-dioxaoctyl)-amine in 300 g of anisole were introduced into a 1 liter round-bottomed flask equipped as in Example 1. After refluxing for 6 hours, the degree of conversion was 75%.

COMPARATIVE EXAMPLE

The above procedure was repeated, but without the tris-(3,6-dioxaoctyl)-amine and a degree of conversion of only 1.5% was attained.

EXAMPLE 11

Preparation of 1-(2'-methylphenoxy)-4-trifluoromethylbenzene,

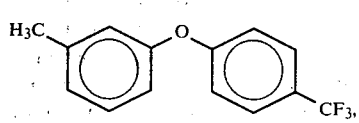

from p-chlorotrifluoromethylbenzene,

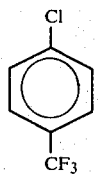

and sodium metacresolate,

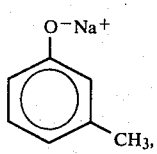

in the presence of cuprous chloride, CuCl, and tris-(3,6-dioxaheptyl)-amine.

65 g (0.5 mol) of sodium m-cresolate, 90.25 g (0.5 mol) of p-chlorotrifluoromethylbenzene, 5 g (0.005 mol) of cuprous chloride, 18 g (0.056 mol) of tris-(3,6-dioxaheptyl)-amine and 300 g of anisole were introduced into a 1 liter round-bottomed flask equipped as in Example 1. After refluxing for 6 hours at 150° C., the degree of conversion had reached 75%.

COMPARATIVE EXAMPLE

Without the tris-(3,6-dioxaheptyl)-amine, repeating the above procedure resulted in a degree of conversion of only 3.4% after 6 hours.

EXAMPLE 12

Preparation of meta-phenoxytoluene,

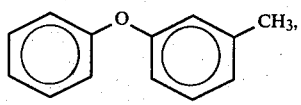

from sodium meta-cresolate and potassium meta-cresolate,

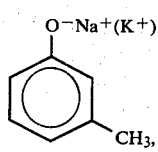

and chlorobenzene,

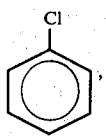

in the presence of cuprous chloride and tris-(3,6-dioxaoctyl)-amine.

14.3 kg (132.4 mols) of m-cresol, 75 Kg (667 mols) of chlorobenzene, 9.24 kg of 36° Bé strength sodium hydroxide solution and 4.48 kg of 50% strength potassium hydroxide solution were introduced into a 100 liter stainless steel apparatus equipped with a distillation column. Salt formation was carried out by distilling the water as an azeotrope. As soon as the temperature of the mixture had reached 132° C., 1.6 kg (16 moles) of cuprous chloride and 2 kg (5.5 mols) of tris-(3,6-dioxaoctyl)-amine were introduced and an atmosphere of hydrogen was established. After refluxing for 5 hours at 135° C., the degree of conversion had reached 88% and the yield had reached 93%.

After cooling to 80° C., the salts formed were extracted with acid water and the organic mixture was then distilled in order to remove the excess chlorobenzene, the unreacted cresol and then the m-phenoxy-toluene. 21.6 kg of m-phenoxytoluene were thus obtained, this being a yield of 89%.

EXAMPLE 13

2.88 g, i.e., 0.02 mol, of the sodium salt formed form meta-hydroxybenzaldehyde, 60 g of bromobenzene, 0.2 g (0.002 mol) of CuCl and 0.15 g of tris-(3,6-dioxaoctyl)-amine were introduced into a 100 cm$^3$ Erlenmeyer flask which was equipped with a magnetic stirring bar and was maintained under a nitrogen atmosphere. The mixture was heated at 150° C. for 8 hours. The reaction yield with respect to the meta-phenoxybenzaldehyde was 75%.

COMPARATIVE EXAMPLE

The degree of conversion with respect to meta-phenoxybenzaldehyde was only 1% when the above process was carried out without adding the tris-(3,6-dioxaoctyl)-amine.

EXAMPLE 14

Preparation of tris-(3,6-dioxaoctyl)-amine:

(a) 450 g (5 mols) of 2-ethoxyethanol were introduced into a one liter three-necked round-bottomed flask equipped with a mechanical stirrer, a thermometer and a condenser. 23 g (1 mol) of sodium were added over the course of 3 hours, while the temperature of the mixture was maintained at 40° C.

(b) 51.6 g (i.e., 0.215 mol) of tris-(2-chloroethyl)-amine hydrochloride were added to the above mixture (a). The mixture was subsequently heated at the reflux temperature of the 2-ethoxyethanol for 12 hours and the solvent was then distilled under reduced pressure. The excess sodium 2-ethoxyethanolate was neutralized by adding 12 cm$^3$ of aqueous HCl (10 N) thereto. The sodium chloride was filtered off and the solution was distilled. The tris-(3,6-dioxaoctyl)-amine distilled between 200° C. and 210° C. under a pressure of 1 mm Hg. The yield was 68%.

EXAMPLE 15

Preparation of tris-(3,6-dioxaheptyl)-amine:

(a) 380 g (5 mols) of 2-methoxyethanol were introduced into a one liter three-necked round-bottomed flask equipped with a mechanical stirrer, a thermometer and a condenser. 23 g (1 mol) of sodium were added over the course of 3 hours, while the temperature of the mixture was maintained at 40° C.

(b) 51.6 g (i.e., 0.215 mol) of tris-(2-chloroethyl)-amine hydrochloride were added to the above mixture (a). The mixture was subsequently heated at the reflux temperature of the 2-methoxyethanol (125° C.) for 12 hours and the solvent was then distilled under reduced pressure. The excess sodium 2-methoxyethanolate was neutralized by adding 11.6 cm$^3$ of aqueous HCl (10 N) thereto. The sodium chloride was filtered off and the solution was distilled.

EXAMPLE 16

Preparation of tris-(3,6,9-trioxadecyl)-amine:

600 g, i.e., 5 mols, of diethylene glycol monomethyl ether (3,6-dioxaheptan-1-ol) were introduced into a 1 liter three-necked round-bottomed flask equipped with a mechanical stirrer, a condenser and a thermometer, and 23 g (1 mol) of sodium were then introduced in small portions in order to form sodium 3,6-dioxaheptanolate.

When the sodium had been totally converted, 51.8 g (i.e., 0.215 mol) of tris-(2-chloroethyl)-amine hydrochloride were added thereto. The mixture was heated at 13° C. for 8 hours, under stirring, and then cooled, and the excess sodium alcoholate was neutralized with a 10% aqueous solution of hydrochloric acid. The 3,6-dioxaheptan-1-ol was removed by distillation at 130° C. under a pressure of 20 mm Hg. The resulting mixture was filtered in order to remove the sodium chloride and the product was then distilled. 83 g of tris-(3,6,9-trioxadecyl)-amine, which distilled at 189° C. under a pressure of 0.1 mm Hg, were thus obtained.

While the invention has been described in terms of various preferred embodiments, the skilled artisan will appreciate that various modifications, substitutions, omissions, and changes may be made without departing from the spriit thereof. Accordingly, it is intended that the scope of the present invention be limited solely by the scope of the following claims.

What is claimed is:

1. In a process for the preparation of a diaryl ether by reacting an unactivated halobenzene with an alkali metal phenolate in the presence of a copper catalyst, the improvement which comprises conducting said reaction in the presence of an effective amount of at least one tertiary amine sequestering agent having the formula:

$$N\text{-}[CHR_1\text{---}CHR_2\text{---}O\text{---}CHR_3\text{---}CHR_4\text{---}O]_n R_5]_3 \quad (I)$$

in which n is an integer which is greater than or equal to 0 and less than or equal to about 10, $R_1$, $R_2$, $R_3$ and $R_4$, which are identical or different, each represent a hydrogen atom or an alkyl radical having from 1 to 4 carbon atoms and $R_5$ represents an alkyl or cycloalkyl radical having from 1 to 12 carbon atoms, a phenyl radical or a radical —$C_mH_{2m}$—$\phi$— or $C_mH_{2m+1}$—$\phi$—, wherein $\phi$ is phenyl and in which m is between 1 and 12.

2. The process as defined by claim 1, wherein the reaction is conducted in the presence of an inert solvent.

3. The process as defined by claim 1, wherein the reaction is conducted in the absence of solvent.

4. The process as defined by claims 2 or 3, wherein the formula (I), $R_1$, $R_2$, $R_3$ and $R_4$ are each hydrogen or methyl.

5. The process as defined by claims 1 or 2, wherein the formula (I), n is an integer which is greater than or equal to 0 and less than or equal to 6.

6. The process as defined by claims 1 or 2, wherein the formula (I), $R_5$ is an alkyl radical having from 1 to 4 carbon atoms.

7. The process as defined by claims 1 or 2, wherein the formula (I), $R_1$, $R_2$, $R_3$ and $R_4$, which are identical or different, are each hydrogen or methyl, n is an integer which is greater than or equal to 0 and less than or equal to 6 and $R_5$ is an alkyl radical having from 1 to 4 carbon atoms.

8. The process as defined by claim 7, wherein the tertiary amine of the formula (I) is tris-(3,6-dioxaheptyl)-amine of the formula:

$$N\text{---}(CH_2\text{---}CH_2\text{---}O\text{---}CH_2\text{---}CH_2\text{---}O\text{---}CH_3)_3.$$

9. The process as defined by claim 7, wherein the tertiary amine of the formula (I) is tris-(3,6,9-trioxadecyl)-amine of the formula:

$$N\text{---}(CH_2\text{---}CH_2\text{---}O\text{---}CH_2\text{---}CH_2\text{---}O\text{---}CH_2\text{---}CH_2\text{---}O\text{---}CH_3)_3.$$

10. The process as defined by claim 7, wherein the tertiary amine of the formula (I) is tris-(3,6-dioxaoctyl)-amine of the formula:

$$N\text{---}(CH_2\text{---}CH_2\text{---}O\text{---}CH_2\text{---}CH_2\text{---}O\text{---}C_2H_5)_3.$$

11. The process as defined by claim 1, wherein the tertiary amine of the formula (I) is selected from the group consisting of tris-(3-oxabutyl)-amine, tris-(3,6-dioxaheptyl)-amine, tris-(3,6,9-trioxadecyl)-amine, tris-(3,6-dioxaoctyl)-amine, tris-(3,6,9-trixaundecyl)-amine, tris-(3,6-dioxanonyl)-amine, tris-(3,6,9-trioxadodecyl)-amine, tris-(3,6-dioxadecyl)-amine, tris-(3,6,9-trioxatridecyl)-amine, tris-(3,6,9,12-tetraoxatridecyl)-amine, tris-(3,6,9,12,15,18-hexaoxanonadecyl)-amine, tris-(3,6-dioxa-4-methylheptyl)-amine and tris-(3,6-dioxa-2,4-dimethylheptyl)-amine.

12. The process as defined by claims 2 or 3, wherein the halobenzene reacted has the structural formula:

in which n is greater than or equal to 1 and less than or equal to 6, the radical or radicals X, which are identical or different, are selected from the group consisting of Cl, Br and I, and the radical or radicals $R_6$, which are identical or different, are selected from the group consisting of hydrogen, alkyl and cycloalkyl radicals having from 1 to 12 carbon atoms, alkenyl radicals having from 3 to 12 carbon atoms, radicals of the formulae $C_mH_{2m+1}$—$\phi$—, $C_mH_{2m-1}$—$\phi$— and $\phi$—$C_mH_{2m}$—, in which m is an integer between 1 and 12 and $\phi$ comprises a phenyl moiety, alkoxy radicals having from 1 to 12 carbon atoms and phenoxy radicals, the radicals —$C_mH_{2m}$—OH and —$C_mH_{2m}$OR, in which m is an integer between 1 and 12 and in which R is an alkyl radical having from 1 to 12 carbon atoms or a phenyl radical, alkylthio radicals having from 1 to 12 carbon atoms and phenylthio radicals, the radicals $C_pH_{2p+1-q}F_q$, p being between 1 and 4 and q being between 3 and 9, the radicals

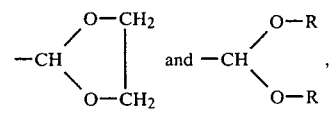

in which R is an alkyl radical having from 1 to 12 carbon atoms or a phenyl radical, and the radicals —$NO_2$, —$SO_3M$, —CN, —$CO_2M$, —$CO_2R$, —COR and —COH, in which M represents an alkali metal and in which R represents an alkyl radical having from 1 to 12 carbon atoms or a phenyl radical, with the proviso that if $R_6$ is ortho- or para- to a substituent X, then same cannot be either $-NO_2$, $-SO_3M$, $-CN$, $-CO_2M$, $-CO_2R$, $-COR$ or $-SO_2R$ as defined above.

13. The process as defined by claim 12, wherein the phenolate reacted is selected from the group consisting of those having the structural formulae:

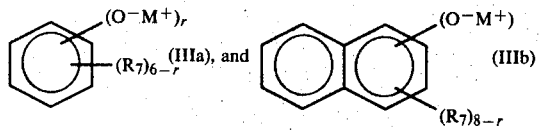

in which r is equal to 1 or 2, the cation or cations $M^+$, which are identical or different, are selected from the group consisting of $Li^+$, $Na^+$ and $K^+$, and the radical or radicals $R_7$, which are identical or different, are selected from the group consisting of hydrogen, alkyl and cycloalkyl radicals having from 1 to 12 carbon atoms, alkenyl radicals having from 3 to 12 carbon atoms, radicals of the formulae $C_mH_{2m+1}\phi-$, $C_mH_{2m-1}\phi$ and $\phi-C_mH_{2m}-$, in which m is an integer between 1 and 12 and $\phi$ comprises a phenyl moiety, alkoxy radicals having from 1 to 12 carbon atoms and phenoxy radicals, the radicals $-C_mH_{2m}-OH$ and $-C_mH_{2m}OR$, in which m is an integer between 0 and 12 and in which R is an alkyl radical having from 1 to 12 carbon atoms or a phenyl radical, alkylthio radicals having from 1 to 12 carbon atoms and phenylthio radicals, the radicals $C_pH_{2p+1-q}F_q$, p being between 1 and 4 and q being between 3 and 9, the radicals

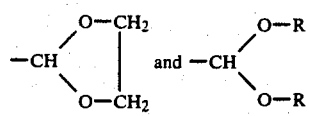

in which R is an alkyl radical having from 1 to 12 carbon atoms or a phenyl radical, the radicals Cl and F and the radicals $-NO_2$, $-NH_2$, $-NHR$, $-NRR$, $-SO_2M$, $-CN$, $-CO_2M$, $-CO_2R$, $-COR$, $-COH$ and $-SO_2R$, in which M represents an alkali metal and in which R represents an alkyl radical having from 1 to 12 carbon atoms or a phenyl radical.

14. The process as defined by claim 13, the phenolate having the structural formula (IIIa).

15. The process as defined by claim 13, the phenolate having the structural formula (IIIb).

16. The process as defined by claim 13, the copper catalyst being selected from the group consisting of CuCl, CuBr, CuI, $CuOCOCH_3$ and $Cu_2O$.

17. The process as defined by claim 2, wherein the reaction is conducted in the presence of a solvent selected from the group consisting of diphenyl ether, anisole, toluene, xylene, glycol polyether and benzene.

18. The process as defined by claims 2 or 3, wherein the amount of the tertiary amine present is such that the molar ratio of the copper catalyst thereto is between about 0.05 and 10.

19. The process as defined by claim 18, wherein said molar ratio is between about 0.1 and 5.

20. The process as defined by claim 1, wherein the reaction is conducted at a temperature between about 50° C. and about 200° C.

21. The process as defined by claim 20, wherein the reaction is conducted at a temperature between about 100° and about 180° C.

22. The process as defined by claim 1 for the preparation of meta-phenoxytoluene by reacting sodium meta-cresolate with chlorobenzene, in the presence of cuprous chloride, said reaction being conducted in the presence of a tertiary amine selected from the group consisting of tris-(3,6-dioxaoctyl)-amine and tris-(3,6-dioxaheptyl)-amine.

23. The process as defined by claim 1 for the preparation of meta-phenoxytoluene by reacting sodium phenolate with 3-chlorotoluene, in the presence of cuprous chloride, said reaction being conducted in the presence of tris-(3,6-dioxaoctyl)-amine.

24. The process as defined by claim 2 for the preparation of meta-phenoxybenzonitrile by reacting 3-chlorobenzonitrile with sodium phenolate, in the presence of cuprous chloride, said reaction being conducted in the presence of tris-(3,6-dioxaoctyl)-amine and in a solvent selected from the group consisting of anisole and diphenyl ether.

25. The process as defined by claim 2 for the preparation of methyl meta-phenoxybenzoate by reacting sodium phenolate with methyl meta-chlorobenzoate, in the presence of cuprous chloride, said reaction being conducted in the presence of tris-(3,6-dioxaoctyl)-amine in anisole.

26. The process as defined by claim 1 for the preparation of meta-phenoxybenzaldehyde by reacting the sodium salt of meta-hydroxybenzaldehyde with bromobenzene, in the presence of cuprous chloride, said reaction being conducted in the presence of tris-(3,6-dioxaoctyl)-amine.

* * * * *